United States Patent [19]
Hardy et al.

[11] Patent Number: 5,496,728
[45] Date of Patent: Mar. 5, 1996

[54] ENCAPSULATION OF LIQUIDS IN MICRO-ORGANISMS

[75] Inventors: Frederick E. Hardy, Ponteland; Alan D. Willey, Sandyford, both of Great Britain; Stefano Scialla, Rome, Italy

[73] Assignee: The Procter & Gamble Company, Cincinnati, Ohio

[21] Appl. No.: 244,798

[22] PCT Filed: Dec. 1, 1992

[86] PCT No.: PCT/US92/10391

§ 371 Date: Jun. 13, 1994

§ 102(e) Date: Jun. 13, 1994

[30] Foreign Application Priority Data

Dec. 13, 1991 [EP] European Pat. Off. .............. 91870208

[51] Int. Cl.$^6$ .............. B01J 13/02; C11D 3/395; C12N 1/16; C12N 1/18
[52] U.S. Cl. .............. 435/255.1; 435/252.1; 435/255.2; 252/186.28; 252/186.38; 252/186.41; 428/402.2; 264/4.1
[58] Field of Search .............. 435/255.1, 255.2, 435/252.1; 252/95, 186.28, 186.38, 186.41; 264/4.1; 428/402.2

[56] References Cited

U.S. PATENT DOCUMENTS

| | | |
|---|---|---|
| 1,056,540 | 3/1913 | Hentschel . |
| 2,031,668 | 2/1936 | Reich . |
| 3,615,654 | 10/1971 | Ayukawa et al. .............. 426/262 |
| 3,925,234 | 12/1975 | Hachmann et al. .............. 252/97 |
| 3,951,594 | 4/1976 | Smolens .............. 252/95 |
| 4,001,480 | 1/1977 | Shank .............. 435/182 |
| 4,025,453 | 5/1977 | Kravetz et al. .............. 252/95 |
| 4,244,834 | 1/1981 | Schwalley et al. .............. 252/106 |
| 4,526,583 | 7/1985 | Gioffre .............. 252/90 |
| 4,647,536 | 3/1987 | Mosbagh et al. .............. 435/177 |
| 4,790,238 | 12/1988 | Hsu .............. 426/15 |
| 4,822,534 | 4/1989 | Lencki et al. .............. 264/4.3 |
| 4,877,605 | 10/1989 | Hendricks .............. 424/65 |
| 5,078,904 | 1/1992 | Behan et al. .............. 252/8.6 |

FOREIGN PATENT DOCUMENTS 0242135 10/1987 European Pat. Off. .

OTHER PUBLICATIONS

Derwent Abs. J50006783 (Hitachi Ltd.) AN–75–26653w/16 Jan. 23, 1975.
Derwent Abs J51136887 (Mitsubishi Gas) AN–77–02970y/02 Nov. 26, 1976.
APS ABS Japan Patent 55–111058 OUBI Feb. 1979.
Derwent Abs EP–414282 (Feb. 2, 1991) Behan et al AN–91–059517/09.

*Primary Examiner*—Herbert J. Lilling
*Attorney, Agent, or Firm*—K. W. Zerby; T. D. Reed; J. C. Rasser

[57] ABSTRACT

Yeast or other micro-organism cells for use in the encapsulation of liquids (e.g. liquid bleach activators for use in laundry detergent compositions) are deodorised by treatment with a peroxygen bleach, e.g. hydrogen peroxide.

6 Claims, No Drawings

ENCAPSULATION OF LIQUIDS IN MICRO-ORGANISMS

FIELD OF THE INVENTION

The present invention relates to a method of reducing the odour of micro-organism cells. The invention also relates to the use of the resultant deodorised cells in a process for encapsulating a material, in which micro-organism cells are contacted with the said material, which material is in liquid form, whereby the said material is absorbed through the micro-organism cell wall and retained within the micro-organism cells. The invention also relates to liquids that have been encapsulated in that manner.

BACKGROUND TO THE INVENTION

The encapsulation of materials within micro-organism cells is well known. In EP-B-0,085,805 (Dunlop Limited), a method of encapsulation is described in which the micro-organism is contacted with an organic lipid-extending substance that is a solvent, or a micro-dispersing medium, for the material to be encapsulated, and simultaneously and/or subsequently the micro-organism is contacted with the material to be encapsulated, said material being employed as a solution or micro-dispersion in the organic lipid-extending substance, or in a further organic lipid-extending substance or in a liquid that is miscible with the first-mentioned lipid-extending substance, whereby both the organic lipid-extending substance and the material to be encapsulated are taken into and retained passively within the micro-organism. Suitable micro-organisms include yeasts and suitable lipid-extending substances include aliphatic alcohols, esters, aromatic hydrocarbons and hydrogenated aromatic hydrocarbons. An example of a material that can be encapsulated is a leuco dye suitable for use in "carbonless" copy paper. A stated advantage of the method described in that European patent is that, in contrast to certain earlier proposals (cf. U.S. Pat. No. 4,001,480 and FR-A-2,179,528), use may be made of micro-organisms having a natural lipid content of less than 40 percent by weight, without the need to employ a plasmolyser.

EP-A-0,242,135 (AD2 Limited) discloses a method of producing an encapsulated material by contacting the material in liquid form with a grown intact micro-organism having a microbial lipid content of less than 40 percent by weight. The encapsulatable material must be capable of diffusing into the microbial cell without causing total lysation thereof and the treatment of the micro-organism is carried out in the absence of an organic lipid-extending substance as solvent or microdispersant for the encapsulatable material and in the absence of a plasmolyser. The material is absorbed by the micro-organism—typically a yeast—by diffusion across the microbial cell wall and is passively retained within the micro-organism. A wide variety of encapsulatable materials are mentioned, including essential oils used as flavours or fragrances, leuco dyes, vitamins, detergents such as lauryl ether sulfate, food colourants, and pesticides and the like.

EP-A-0,414,282 (Quest International) discloses bleach compositions, including laundry detergents, laundry bleaches and dishwashing or scouring products, that contain a perfume whereas EP-A-0,414,283 (Quest International) discloses fabric-softening compositions that contain a perfume. In both cases, the perfume is encapsulated in micro-organism cells according to the conventional methods, as described in U.S. Pat. No. 4,001,480 or EP-A-0,242,135.

A problem that arises when using micro-organism cells for encapsulation purposes is that they may have a disagreeable odour and possibly also an unpleasing colour and may therefore diminish the acceptability of the encapsulated products, or compositions containing them, to consumers.

SUMMARY OF THE INVENTION

It has now been found that micro-organism cells may be at least partially deodorised by treatment with a peroxygen bleach whilst leaving the cells at least largely intact and hence suitable for encapsulation purposes.

The present invention, in one of its aspects, accordingly provides a method of reducing the odour of micro-organism cells, characterised in that the said cells are treated with a peroxygen bleach.

The invention also provides, in another of its aspects, a process for encapsulating a material in which micro-organism cells are contacted with the said material, which material is in liquid form, whereby the said material is absorbed through the micro-organism cell wall and retained within the micro-organism cells, characterised in that the micro-organism cells are also treated with a peroxygen bleach.

DESCRIPTION OF EXEMPLARY EMBODIMENTS

Although bacteria and algae may be suitable, preferred micro-organisms are fungi, especially filamentous fungi, e.g. *Aspergillus niger*, and more especially the yeasts.

Examples of yeasts which may be used in the present invention are *Lipomyces* species, such as *L. lipofer* and *L. starkeyi*, *Trichosporon* species, such as *T. pullulans* and *T. cutaneum*, *Candida* species such as *C. currata* and *C. utilis*, *Kluvveromyces fragilis* and *Saccharomyces cerevisiae*.

Usually, use will be made of micro-organism cells in grown form, i.e. that have been harvested from a culture medium. The cells should be intact, that is to say not have undergone any significant lysation, and are preferably of large size, typically with an average diameter for the cell of from 5 to 20 µm. It is also desirable that the cells should not undergo lysation before or during the encapsulation step.

A micro-organism will normally be chosen that under the conditions of the intended use will disintegrate or undergo sufficient disruption or permit diffusion of its contents so that the encapsulated liquid will be released at the appropriate point of application.

In accordance with this invention, the micro-organism cells are treated with a peroxygen bleach, for example peracids (including so-called 'low-activity' peracids), such as peroxymonosulfuric acid, m-chloroperbenzoic acid, diperisophthalic acid and monoperphthalic acid, and their derivatives, e.g. salts such as potassium monopersulfate ("oxone") or magnesium monoperoxyphthalate ("H48"). Compounds that release hydrogen peroxide when dissolved in water come into consideration, especially those that are commercially available; these includes such salts as perborates, notably sodium perborate, and such adducts as percarbonates. At present, however, the preferred peroxygen bleach is hydrogen peroxide ($H_2O_2$).

Although the applicant does not wish to be bound by any theory, it is believed that the peroxygen bleach attacks the amine centres in the micro-organism. Generally, the treatment with the peroxygen bleach should be carried out under conditions that achieve a significant reduction in, or even complete removal of, the characteristic micro-organism odour and/or colour without being so severe as to cause any significant lysation or disruption of the cell walls (which would impair the effectiveness of the micro-organism as an encapsulation material). Generally, the micro-organism is treated with an aqueous solution of the peroxygen bleach, especially one containing the peroxygen bleach at a concentration of from 0.01 to 10%, more preferably from 0.02 to 5% and most preferably from 0.1 to 2%, w/v. Relative to the weight of micro-organism, the amount of peroxygen bleach is usually 0.02 to 100%, preferably 0.04 to 50% and more preferably 0.1 to 20% by weight. The solution of peroxygen bleach is preferably prepared in deionised water.

The peroxygen bleach-containing treatment solution is preferably alkaline and will typically contain an alkali usually an alkali metal or alkaline earth metal hydroxide or carbonate, preferably sodium hydroxide—at a concentration from 0 to 2.0M, preferably from 0.01 to 1.0M, more preferably from 0.05 to 0.5M. Simply buffering the solution at high pH may also be considered.

It has also proved advantageous for the peroxygen bleach-containing solution to contain sodium silicate, preferably in an amount from 20 to 60 g/l, typically from 30 to 50 g/l. The sodium silicate is useful as a filtering aid, is a source of alkalinity, acts as a defoaming agent and provides some control over heavy metals that might decompose the peroxygen bleach. Of course, other silicates, e.g. other alkali metal silicates, come into consideration for use with or instead of the sodium silicate, as do filtration aids, such as Kieselguhr or Celite, and chelating agents, such as phosphonates, ethylenediamine tetraacetic acid (EDTA) and sodium tripolyphosphate (STP).

Normally, up to 250 g, typically 50 to 150 g, of micro-organism is employed per liter of the peroxygen bleach-containing solution. The treatment is conveniently effected by suspending the micro-organism in the treating solution and gently stirring the suspension. Suitable durations for the treatment and suitable temperatures at which it may be carried out can be determined by simple trials; in general, it has been found adequate for the suspension to be stirred for from 5 minutes to 4 hours, preferably from 30 minutes to 2 hours and typically for about 1 hour, at a temperature of from 0° to 100° C., preferably from 10° to 50° C. and typically at room temperature. The treated micro-organism is then separated from the treating solution by any convenient method, e.g. centrifugation, and is generally dried, e.g. by freeze drying, before further use.

Although the primary purpose in treating the micro-organism cells with the peroxygen bleach is to reduce or eliminate any odour of the micro-organism, the treated micro-organism may also be referred to hereinafter as a "bleached" micro-organism; it has been found that the reduction in odour is often accompanied by a lightening of the colour of the micro-organism cell material.

The treated micro-organism may be employed for the encapsulation of a wide variety of encapsulatable materials using any of the methods known in principle from the prior art, e.g. the method described in U.S. Pat. No. 4,001,480, in EP-B-0,085,805 or, preferably, in EP-A-0,242,135 (the teaching in each of which is incorporated herein by reference).

The material to be encapsulated should be in liquid form under the conditions at which encapsulation is carried out. Materials that are not themselves liquid under those conditions may be used in the form of a solution or micro dispersion in a suitable solvent or dispersant, usually a solvent that is immiscible with lipid that may be present in the micro-organism. Suitable solvents include $C_1$–$C_4$ alcohols, e.g. methanol, ethanol or isopropanol, and the solvent may be removed by evaporation after the encapsulation treatment. It is also possible, and sometimes preferred, to carry out the encapsulation process in the presence of water.

Although it is preferred to treat the micro-organisms with the peroxygen bleach before encapsulation is effected, it is possible in principle to effect such treatment during or even after the encapsulation step. Thus, for example, encapsulation could be effected from a system containing both the peroxygen bleach in aqueous solution and the material to be encapsulated, provided that the material to be encapsulated were compatible with that bleach.

The present invention is particularly advantageous in the encapsulation of bleach activators used in cleaning compositions, for example heavy duty or general purpose laundry detergent compositions, bleaching compositions, dishwashing compositions and hard-surface or other cleaning products.

Such bleach activators are commonly susceptible to attack by moisture, leading to hydrolysis or premature perhydrolysis, the products of which are liable to damage other ingredients in the cleaning composition. Suitable bleach activators are disclosed in U.S. Pat. Nos. 4,179,390 (Spadini et al.), 4,412,934 (Chung et al.) and 4,915,854 (Mao et al.)

The present invention is illustrated in and by the following examples.

Example 1

(a) Yeast Treatment 100 g of baker's yeast (*Saccharomyces cerevisiae*) were suspended in one liter of a 0.2 molar solution of sodium hydroxide in water containing 40 g of sodium silicate. Hydrogen peroxide was added until its concentration reached 1% w/v and the resultant suspension was then gently stirred for one hour at room temperature. The yeast was then removed by centrifugation and freeze dried.

(b) Encapsulation

One part by weight of the bleached yeast obtained according to the above-described treatment (a) was suspended in three parts of water and stirred at 60° C. for one hour. 0.6 parts of the material to be encapsulated, namely acetyl triethyl citrate, was then added and the suspension was stirred for 6 hours at 45° C. The yeast cells were then removed by centrifugation and freeze dried. The resultant yeast-encapsulated acetyl triethyl citrate was suitable for incorporation into detergent formulations as a bleach activator.

Example 2

A number of samples of bleached yeast micro-capsules were prepared using the process described above in Example 1(a) but with certain variations in the yeast concentration, alkalinity, the presence or absence of sodium silicate, and the concentration of hydrogen peroxide. The samples were assessed for yeast odour and for the amount of foaming produced during the hydrogen peroxide treatment. The results are summarised in the following table (in which sample 5 indicates the sample obtained by the process according to Example 1(a)).

TABLE 1

| Sample | Yeast Conc. (g/l) | Alkalinity (M) | Sodium Silicate (+/−) | $H_2O_2$ (%) | Yeast Odour (1–5) | Foaming (1–5) |
| --- | --- | --- | --- | --- | --- | --- |
| 1 | 250 | — | − | 10 | 1 | 5 |
| 2 | 100 | — | − | 1 | 1 | 5 |
| 3 | 100 | 2 | + | 10 | 1 | 1 |
| 4 | 100 | 1 | + | 1 | 1 | 1 |
| 5 | 100 | 0.2 | + | 1 | 1 | 2 |
| 6 | 100 | 0.05 | + | 1 | 3 | 5 |

Key
Odour
1 = Best, i.e. little or no odour
5 = Worst, i.e. odour approximately equal to starting material.
Foaming
1 = Best, i.e. little foaming
5 = Worst, i.e. excessive foaming For the yeast cells to be useful for encapsulation purposes, the cell membrane must be intact. Microscopy showed that this was only the case for Samples 5 and 6. Sample 5 was preferred to Sample 6, in that it exhibited a lower odour and lower foaming.

Example 3

Bleached yeast micro-capsules containing the liquid bleach activator, acetyl triethyl citrate, which micro capsules had been prepared according to the process of Example 1(b), were blended into a standard detergent composition and stored in sealed cartons under stressed storage conditions (32° C. and 80% humidity). For comparison purposes, a similar composition was prepared containing the liquid bleach activator encapsulated in unbleached yeast micro-capsules prepared according to the prior art (EP-A-0,242,135). A further comparison composition was prepared containing, instead of the encapsulated liquid bleach activator, a conventional activator, tetraacetyl ethylene diamine (TAED), in particulate form. The comparison compositions were stored in sealed cartons under the stressed storage conditions specified above.

The compositions were sampled after certain periods of time, the samples being analyzed in order to determine how much of the bleach activator (acetyl triethyl citrate or TAED, as the case may be) remained (expressed as a percentage of the original content). Specifically, the analysis was effected by dissolving the sample, analyzing for peracid and comparing that result with the expected result for 100% active. The results are shown in the following table.

TABLE 2

| Time Weeks | Unbleached % remaining | Bleached % remaining | TAED % remaining |
| --- | --- | --- | --- |
| 0 | 100 | 100 | 100 |
| 2 | 81 | 76 | 98 |
| 5 | 67 | (29) | 67 |
| 8 | 27 | 40 | 61 |

The 5-week result for the bleached capsules is anomalous and is thought to be due to poor dispersion of the product; in particular, caking, which is a problem commonly experienced when using such stressed storage conditions, tends to render dissolution of the product difficult. Overall, the performance of the bleached capsules in preserving the activity of the bleach activator was deemed comparable to the effectiveness of the conventional, unbleached capsules.

It will of course be understood that the present invention has been described above purely by way of example and that modifications of detail can be made within the scope of the invention.

We claim:

1. A method for encapsulating a bleach activator in micro-organism cells for use in laundry compositions, said method comprising the steps of:

(a) deodorizing intact microorganism cells with a peroxygen bleach under conditions whereby the odor of the microorganism cells is reduced while maintaining at least a portion of the deodorized cells intact;

(b) contacting the deodorized microorganism cells from step (a) with a liquid selected from liquid bleach activators and liquids containing solvent and bleach activator under conditions whereby at least a portion of the bleach activator is encapsulated in the intact deodorized microorganism cells; and (c) collecting the microorganism cell-encapsulated bleach activator.

2. The method according to claim 1 wherein the microorganism cells are deodorized under alkaline conditions.

3. The method according to claim 2 wherein the deodorization step (a) further comprises silicate.

4. The method according to claim 1 wherein the peroxygen bleach is hydrogen peroxide.

5. The method according to claim 1 wherein the microorganism cells are selected from the group consisting of yeast cells and fungi cells.

6. A microorganism cell-encapsulated bleach activator composition prepared according to the method of claim 1.

* * * * *